US006841679B2

(12) United States Patent
Rey et al.

(10) Patent No.: US 6,841,679 B2
(45) Date of Patent: Jan. 11, 2005

(54) PROCESS FOR THE PREPARATION OF IMIDAZOPYRIDINES

(75) Inventors: Max Rey, deceased, late of Wallisellen (CH); by Heidedore Hisabeth Rey-Papina, legal representative, Wallisellen (CH); Armin Rossler, Tengen (DE); Giusep Derungs, Zürich (CH); Jae Kyoung Pak, Zurich (CH)

(73) Assignee: Cilag AG, Schaffhausen (CH)

( * ) Notice: Subject to any disclaimer, the term of this patent is extended or adjusted under 35 U.S.C. 154(b) by 0 days.

(21) Appl. No.: 10/344,713

(22) PCT Filed: Aug. 17, 2001

(86) PCT No.: PCT/EP01/09519

§ 371 (c)(1),
(2), (4) Date: Nov. 24, 2003

(87) PCT Pub. No.: WO02/14316

PCT Pub. Date: Feb. 21, 2002

(65) Prior Publication Data

US 2004/0072861 A1 Apr. 15, 2004

(30) Foreign Application Priority Data

Aug. 17, 2000 (EP) .................................. PCT/EP00/08021

(51) Int. Cl.$^7$ ............................................. C07D 471/02
(52) U.S. Cl. ...................... 546/121; 546/112; 546/113
(58) Field of Search ................................ 546/121, 113, 546/112

(56) References Cited

U.S. PATENT DOCUMENTS 4,794,185 A * 12/1988 Rossey et al. ............... 546/121

* cited by examiner

Primary Examiner—Charanjit S. Aulakh
(74) Attorney, Agent, or Firm—Hoffmann & Baron, LLP

(57) ABSTRACT

A compound of the general formula (1), in which: Y denotes hydrogen, a halogen or a $C_{1-4}$ alkyl group; $X_1$ and $X_2$ denote, independently of each other, hydrogen, a halogen, a $C_{1-4}$ alkoxy, $C_{1-6}$ alkyl, $CF_3$, $CH_3S$ $CH_3SO_2$ or $NO_2$ group; and $R_1$ and $R_2$ denote independently of each other, hydrogen or a $C_{1-5}$ alkyl group, with the proviso that $R_1$ and $R_2$ do not both denote hydrogen, or a salt thereof, and is prepared by a multi-step process, the last step of which comprises reducing a compound of the general formula (6), in which Y, $X_1$, $X_2$, $R_1$ and $R_2$ are as defined above with an appropriate reducing agent, such as Zn, and, if desired, converting the compound of formula (1) thus obtained, into a salt. The products of this process are known to have useful pharmacological properties, e.g. as anxiolytics.

8 Claims, No Drawings

PROCESS FOR THE PREPARATION OF IMIDAZOPYRIDINES

The present invention relates to a process for preparing imidazopyridines of the general formula (1)

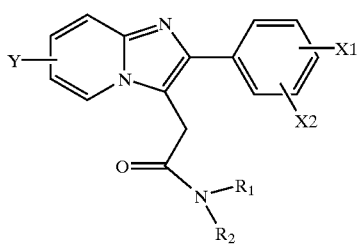

(1)

in which:

Y denotes hydrogen, a halogen or a $C_{1-4}$ alkyl group, $X_1$ and $X_2$ denote, independently of each other, hydrogen, a halogen or a $C_{1-4}$ alkoxy, $C_{1-6}$ alkyl, $CF_3$, $CH_3S$, $CH_3SO_2$ or $NO_2$ group and $R_1$ and $R_2$ denote, independently of each other, hydrogen or a $C_{1-5}$ alkyl group, with the proviso that $R_1$ and $R_2$ do not both denote hydrogen, or salts thereof.

The products of this process are known to have useful pharmacological properties, e.g. as anxiolytics, see European Patent No. 0 050 563. A process for preparing compounds of formula 1 is described in U.S. Pat. No. 4,794,185, Dec. 12, 1988.

The present invention relates to a more efficient process for preparing compounds of formula (1).

In accordance with the present invention, compounds of the general formula (1) can be prepared by reacting a compound of the general formula (2)

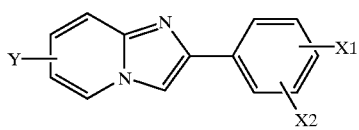

(2)

in which Y, $X_1$ and $X_2$, are as defined above with a compound of the general formula (3)

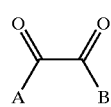

(3)

in which:

A denotes a halogen and B denotes a halogen, a $C_{1-4}$ alkoxy group or an $NR_1R_2$ group in which $R_1$ and $R_2$ are as defined above to form a compound of the general formula (4)

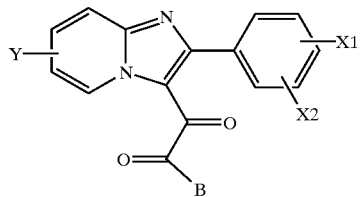

(4)

in which Y, $X_1$, $X_2$ and B are as defined above, and, if B denotes a halogen or a $C_{1-4}$ alkoxy group, reacting the compound of the general formula (4) with a compound of the general formula (5)

(5)

in which $R_1$ and $R_2$ are as defined above to form a compound of the general formula (6)

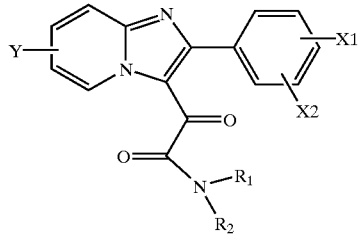

(6)

in which Y, $X_1$, $X_2$, $R_1$ and $R_2$ are as defined above.

To form a compound of formula (1), the compound of formula (6) can be treated with a reducing agent. If desired, the compound of formula (1) thus obtained is converted into a salt.

It will be appreciated that if in formula (3) B denotes an $NR_1R_2$ group in which $R_1$ and $R_2$ are as defined above, compound (6) instead of compound (4) is formed directly by reaction of compound (2) with compound (3).

As set forth above compound (4) is prepared by reacting an imidazopyridine of formula (2) with an oxalic acid derivative of formula (3). This reaction is conveniently carried out in an aprotic organic solvent, for example n-hexane, cyclohexane, acetonitrile, acetone, ethylacetate, toluene, methyl tert. butyl ether or mixtures of these solvents, preferably a mixture of cyclohexane with toluene, at a temperature range from 0–100° C., preferably from 0–10° C., and in the presence of an organic base, for example tertiary alkylamines, pyridine or substituted pyridines, preferably pyridine. If in formula (3) B denotes a halogen or a $C_{1-4}$ alkoxy group, the product (4) thus obtained is subsequently reacted with a primary or secondary amine of formula (5), conveniently at a temperature range from 0–100° C., preferably from 30–40° C. If in formula (3) B denotes an $NR_1R_2$ group, the reaction of compound (2) with compound (3) directly yields a compound of formula (6) instead of compound (4), and no intervening treatment with a compound of formula (5) is necessary.

The compound of formula (6) thus obtained is then reacted with an appropriate reducing agent to form compound (1). This reaction is conveniently carried out in a polar aprotic solvent, for example pyridine, dimethylformamide or acetonitrile, preferably pyridine, in the presence of an organic acid, for example acetic acid, formic acid or toluenesulfonic acid, preferably acetic acid, and of an acylating agent, for example acetic anhydride or acetylchloride, preferably acetic anhydride, at a temperature range from 25–75° C., preferably from 50–55° C. A suitable reducing agent is, for example, Zn.

The compounds of the general formula (6) and their preparation also form part of the present invention.

The following examples illustrate the invention in greater detail.

EXAMPLE 1

Preparation of 6-methyl-N,N-dimethyl-2-(4-methylphenyl)imidazol[1,2-a]pyridine-3-glyoxyacetamide, compound (6)

To a slurry of 10.0 g (45 mmol) of 6-methyl-2-(4-methylphenyl)imidazo[1,2-a]pyridine in a mixture of 20.0 g of toluene and 28.0 g of cyclohexane were added 8.6 (0.068 mmol) of oxalylchloride within 15 minutes at 0–5° C. 3.6 g (45 mmol) of pyridine were added within 5 minutes at 0–5° C. The resulting slurry was heated to 65–70° C. and stirred for 2 hours. Then it was cooled to 30–35° C. and 8.4 g (187 mmol) of dimethylamine were introduced. To the slurry were added 26.0 g of water and 2.3 g of isopropanol. The product was isolated by filtration to afford the title compound in 80% yield.

EXAMPLE 2

Preparation of N,N-dimethyl-2-[6-methyl-2-(4-methylphenyl)imidazo[1,2-a]pyridine-3-yl]acetamide, compound (1)

To a slurry of 150.0 g (0.467 mol) of 6-methyl-N,N-dimethyl-2-(4-methylphenyl)imidazo[1,2-a]pyridine-3-glyoxyacetamide and 105.0 g (1.605 mol) of zinc powder in 443.0 g of pyridine was added a solution of 94.0 g (0.920 mol) of acetic anhydride in 472.5 g of acetic acid within 20–25 minutes at a temperature below 45° C. The suspension was then heated to 50–55° C. and stirred for 25–30 hours. Unreacted zinc was filtered off and the filtrate was subjected to a vacuum distillation. To the remaining oil 455.0 g of 25% aqueous ammonia solution were added. The precipitated solid was collected by filtration and purified by recrystallization in 800.0 g of methylisobutylketone. The title compound was afforded in 65.6% yield.

What is claimed is:

1. A process for preparing compounds of the general formula (6)

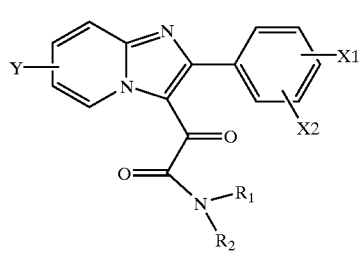

(6)

in which:
Y denotes hydrogen, a halogen or a $C_{1-4}$ alkyl group;
$X_1$ and $X_2$ denote, independently of each other, hydrogen, a halogen or a $C_{1-4}$ alkoxy, $C_{1-6}$ alkyl, $CF_3$, $CH_3S$, $CH_3SO_2$ or $NO_2$ group and $R_1$ and $R_2$ denote, independently of each other, hydrogen or a $C_{1-5}$ alkyl group, with the proviso that $R_1$ and $R_2$ do not both denote hydrogen,
which process comprises reacting a compound of the general formula (2)

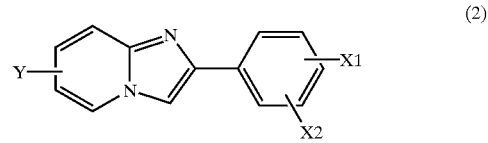

(2)

in which Y, $X_1$ and $X_2$, are as defined above with a compound of the general formula (3)

(3)

in which:
A denotes a halogen and B denotes a halogen, a $C_{1-4}$ alkoxy group or an $NR_1R_2$ group in which $R_1$ and $R_2$ are as defined above to form a compound of the general formula (4)

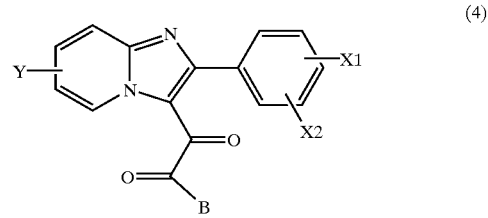

(4)

in which Y, $X_1$ $X_2$ and B are as defined above and, if B denotes a halogen or a $C_{1-4}$ alkoxy group, reacting the compound of formula (4) with a compound of the general formula (5)

(5)

in which $R_1$ and $R_2$ are as defined above.

2. A compound of the general formula (6)

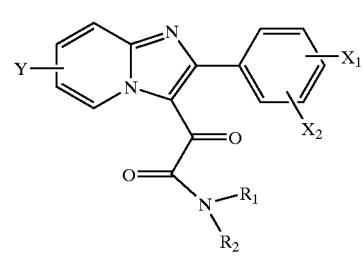

(6)

in which:
Y denotes hydrogen, a halogen or a $C_{1-4}$ alkyl group;
$X_1$ and $X_2$ denote, independently of each other, hydrogen, a halogen or a $C_{1-4}$ alkoxy, $C_{1-6}$ alkyl, $CF_3$, $CH_3S$, $CH_3SO_2$ or $NO_2$ group and $R_1$ and $R_2$ denote independently of each other, hydrogen or a $C_{1-5}$ alkyl group, with the proviso that $R_1$ and $R_2$ do not both denote hydrogen.

3. A process for preparing a compound of the general formula (1)

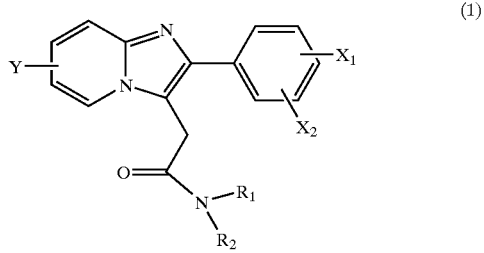

(1)

in which:

Y denotes hydrogen, a halogen or a $C_{1-4}$ alkyl group;

$X_1$ and $X_2$ denote, independently of each other, hydrogen, a halogen, a $C_{1-4}$ alkoxy, $C_{1-6}$ alkyl, $CF_3$, $CH_3S$ $CH_3SO_2$ or $NO_2$ group and $R_1$ and $R_2$ denote independently of each other, hydrogen or a $C_{1-5}$ alkyl group, with the proviso that $R_1$ and $R_2$ do not both denote hydrogen, or a salt thereof which process comprises reducing a compound of the general formula (6)

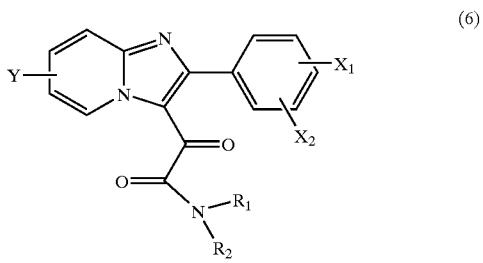

(6)

in which Y, $X_1$, $X_2$, $R_1$ and $R_2$ are as defined above with an appropriate reducing agent and, if desired, converting the compound of formula (1) thus obtained into a salt.

4. A process according to claim 3 wherein the reducing agent is Zn.

5. A process according to claim 3 wherein the reduction is carried out in pyridine, dimethylformamide, dimethylacetamide, acetonitrile or a derivative of any of these, in the presence of acetic acid, formic acid or toluenesulfonic acid and of an acylating agent.

6. A process according to claim 5 wherein the acylating agent is acetic anhydride or acetylchloride.

7. A process according to claim 4 wherein the reduction is carried out in pyridine, dimethylformamide, dimethylacetamide, acetonitrile or a derivative of any of these, in the presence of acetic acid, formic acid or toluenesulfonic acid and of an acylating agent.

8. A process according to claim 7, wherein the acylating agent is acetic anhydride or acetylchloride.

* * * * *